United States Patent [19]

Thornton

[11] Patent Number: 4,706,843

[45] Date of Patent: Nov. 17, 1987

[54] DISPENSING CHAIN OF LOOP LENGTHS OF DENTAL FLOSS OR THE LIKE AND METHOD OF FORMING SAME

[76] Inventor: Theodore W. Thornton, 745 Pacific Ave., Salt Lake City, Utah 84104

[21] Appl. No.: 928,182

[22] Filed: Nov. 7, 1986

[51] Int. Cl.[4] ............................................. B65H 1/00
[52] U.S. Cl. ........................................ 221/48; 221/63; 221/33; 242/137.1; 242/138; 242/146; 206/388; 206/389; 289/1.2; 289/1.5; 132/92 A
[58] Field of Search ...................... 206/388, 63.3, 389; 221/48, 50, 63, 33, 22; 132/91, 92 R, 92 A; 242/137.1, 138, 146, 129; 289/1.2, 1.5, 14, 17, 18.1

[56] References Cited

U.S. PATENT DOCUMENTS

| | | | |
|---|---|---|---|
| 751,214 | 2/1904 | Stoob | 242/146 |
| 1,424,458 | 8/1922 | Fleister | 289/1.5 |
| 1,454,429 | 5/1923 | Dresser | 132/92 A |
| 1,891,497 | 12/1932 | Birkermaier | 289/18.1 |
| 2,702,627 | 2/1955 | Kennison et al. | 206/63.3 |
| 4,084,692 | 4/1978 | Bilweis | 242/137.1 |
| 4,326,630 | 4/1982 | Bacino et al. | 206/63.3 |
| 4,622,986 | 11/1986 | Harris et al. | 132/92 R |
| 4,646,766 | 3/1987 | Stallard | 132/92 A |

Primary Examiner—H. Grant Skaggs
Attorney, Agent, or Firm—Philip A. Mallinckrodt; Robert R. Mallinckrodt

[57] ABSTRACT

For sequentially dispensing individual closed loops of a narrow, easily tied, flexible material, such as dental floss, a chain having such closed loops as respective links thereof is made up by pressing a loop length of the flexible material into substantially rectilinear formation, loosely forming a knot in an end thereof, inserting a loop end of another so-pressed loop length into the loosely formed knot of the first loop length, tightening the knot to provide a slip-free-until-pulled-to-separate-loops joinder between the thus formed loop links and repeating this with additional loop lengths at either or both ends of the first-joined loop length until a chain of desired length is formed. Individual loop links are dispensed by grasping a terminal loop link of the chain and pulling it free of the chain while holding the knot that embraces the unknotted end of the next loop link of the chain. A dispenser is provided for protectively encasing the chain and supplying a V-slot holding member for the knot of a next loop link while a terminal link is being slipped free of the embracing knot of such next loop link.

10 Claims, 6 Drawing Figures

DISPENSING CHAIN OF LOOP LENGTHS OF DENTAL FLOSS OR THE LIKE AND METHOD OF FORMING SAME

BACKGROUND OF THE INVENTION

1. Field

The invention has to do with providing a continuous supply of closed loops of a narrow, easily tied, flexible material, such as dental floss, for dispensing incrementally as relatively short, individual loop lengths, and to dispensers therefor.

2. State of the Art

Material of the kind concerned is normally supplied on or as a spool for unwinding incrementally and separating sequentially as relatively short lengths for use. A very long piece of material is usually wound on a spool or on itself for dispensing through a cut-off device. When a desired length from such a continuous supply of same has been pulled from the spool, it is cut off and put to the desired use.

It has recently become known that dental floss is much easier to use if formed into a rather short, closed loop and held taut about one or more extended fingers of both hands of the user for insertion between and withdrawal from teeth to be cleaned. Moreover, various ways have been suggested for connecting short, individual loops into a continuous length for winding on or as a spool, so that individual loop lengths can be easily dispensed from a sanitary container. However, the proposed ways of connecting individual loops together to form an elongate chain have left much to be desired.

3. Objective

It was a principal objective in the making of the present invention to interconnect individual, performed, loop lengths of dental floss or other narrow, easily tied, flexible material in a simple way as a chain of easily separable links such that the individual loops will remain interconnected during hand or machine winding onto spools or into spool formation and during handling for merchandising purposes and consumer use, but will easily separate, one-by-one sequentially, when the terminal one at the free end of the chain is pulled while holding the next individual link length in the chain-like series of same.

SUMMARY OF THE INVENTION

The foregoing objective is achieved in accordance with the invention by tying a simple knot, such as the well-known overhand or square knot, in one end of mutually adjoining ends of adjoining loop lengths and about the other adjoining end. The knot is tightened about such adjoining end, which remains straight but within the holding embrace of the knot. Thus, each loop length has a straight end portion embraced by a knot in the adjoining end portion of the next loop length, and a knotted end (usually otherwise open) embracing the adjoining straight end portion of the next loop at such knotted end. The terminal loop length at the free end of the chain of loop lengths will be separated under pulling force applied to such terminal loop length when the knotted end of the next loop length in the chain-like series of loop lengths is held.

THE DRAWINGS

The best mode presently contemplated of carrying out the invention in actual practice is shown in the accompanying drawings, in which:

FIG. 1 is an enlarged elevational view of a portion of a chain-like series of individual loop lengths of dental floss tied into individual closed loops, with the loop links of the chain being releasably connected to one another by the knots, intermediate portions being broken out for convenience of illustration;

FIG. 2, a fragmentary view drawn to a larger scale showing how the individual open loop lengths are interconnected as easily separable links by the knots that close the open loop lengths in the chain, the view being taken during loop length interconnection and intermediate portions again being broken out for convenience of illustration;

FIG. 3, a pictoral exploded view of a sanitary dispenser of the invention, showing the spool on which the chain-like supply of interconnected loop lengths of FIG. 1 is wound;

FIG. 4, a fragmentary vertical section taken on the line 4—4 of FIG. 3 and considerably enlarged;

FIG. 5, a view corresponding to that of FIG. 2, but showing a different knot used for both forming and tying individual loop lengths into the chain-like supply of same; and FIG. 6, a fragmentary elevational view looking toward the left in FIG. 3 with the dispenser in unexploded condition and including a sanitary cover in place over the dispensing portion of the dispenser, the open position thereof being shown by dotted lines.

DETAILED DESCRIPTION OF ILLUSTRATED EMBODIMENTS

Figure 1:
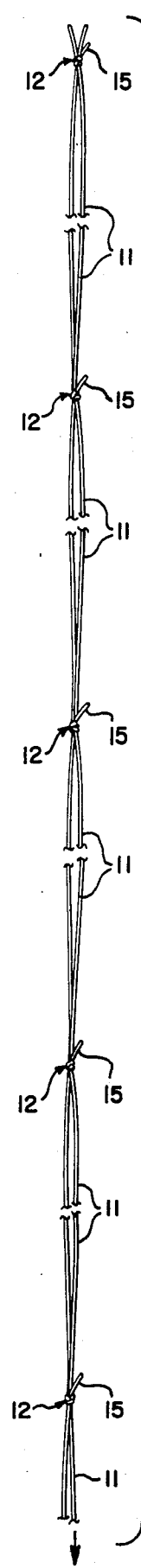
Figure 2:
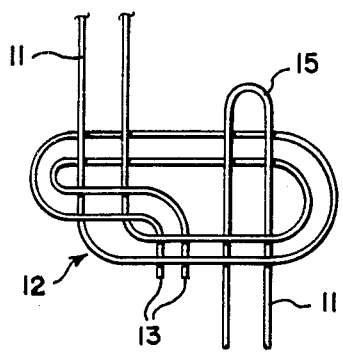
Figure 2:
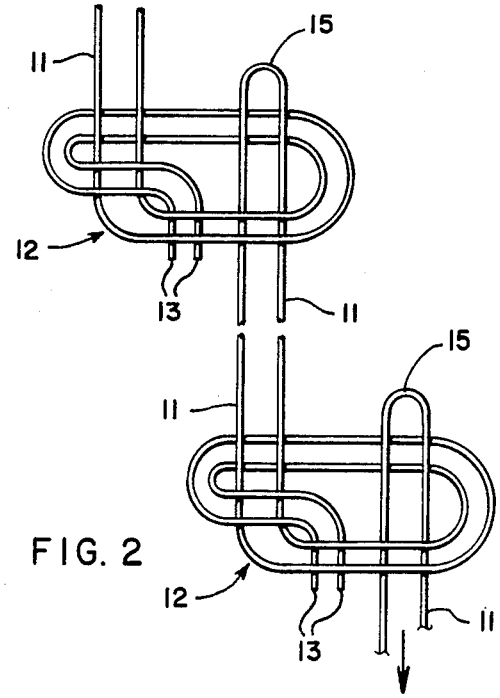
Figure 3:
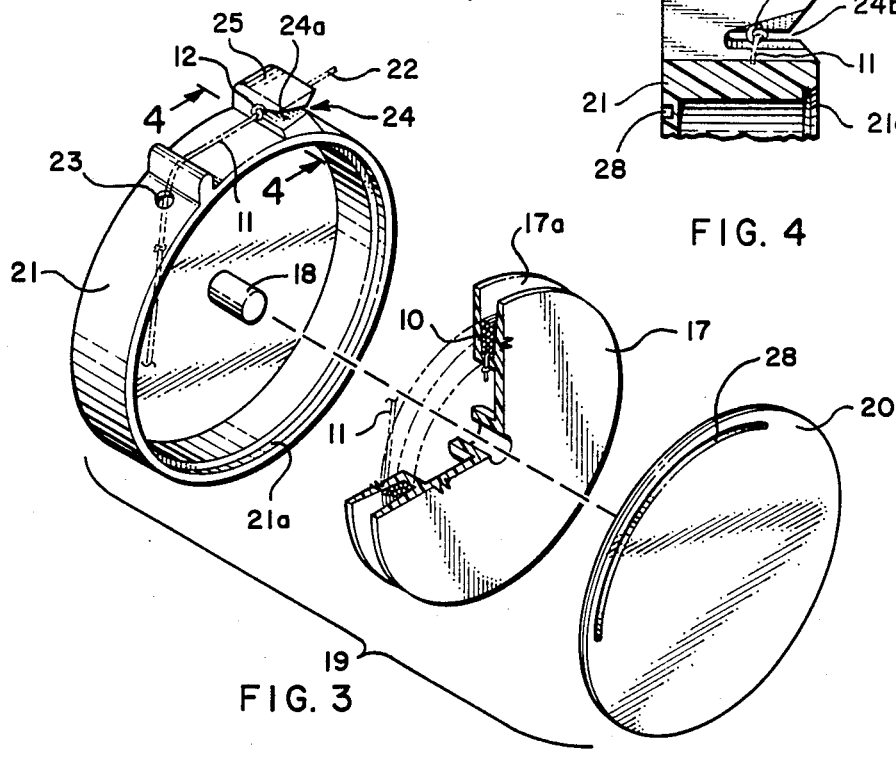

In the form illustrated in FIGS. 1-3, a chain 10 is made up of interconnected, closed loops 11 of dental floss serving as individual links of the chain and providing for convenient and easy, successive separation of the individual closed loop lengths for immediate use when a terminal link is pulled in the direction of the appended arrow.

Each closed loop 11 is preferably made by tying a knot 12 in the open end of a single open loop length of dental floss, which may be done by hand or machine. The knot 12 is preferably tied sufficiently close to the open end of the loop length to leave only very short and stubby tag ends 13. However, closed loops may be performed in any convenient and economical way, for example, as integrally closed loops.

In accordance with the invention, chain 10 is formed by pressing an open loop 11 more or less together rectilinearly, tying the knit 12 loosely in its still open end, by inserting a rectilinear end portion 15 of another so-pressed loop 11 within the loose knot 12 (here shown in FIG. 2 as of overhand type and in FIG. 5 as of square type) formed in the opposite, rectilinear, open end portion of the first loop 11, and by tightening the knot 12 about such inserted rectilinear end portion 15 of the other loop 11. The rectilinear end portion 15 of a third loop 11 is inserted into a similar loose knot 12 formed in the free rectilinear end of the second loop 11, such second knot 12 is tightened, and so on until a chain 10 of the desired length is formed.

Figure 5:
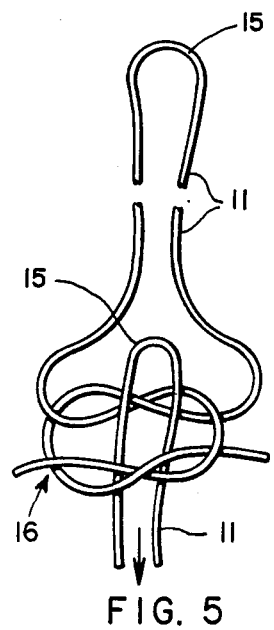

In FIG. 5 is shown a loose square knot 16 in place of the overhand knot 12 as an alternative loop link interconnection arrangement when the loop lengths are formed at the same time the chain is formed.

For dispensing purposes, it is only necessary that chain 10 be held so that the free end (always the end having the link-interconnecting knot) of a terminal loop link 11 may be grasped and pulled to cause the opposite unknotted end embraced by a knot 12 or 16 of the succeeding loop link to slip from the holding embrace.

For marketing purposes, the so formed chain 10 is advantageously wound onto a spool 17, which is placed on a central shaft member 18 of a sanitary dispenser 19 conveniently made of transparent plastic so that the remaining supply of loop links is visible and so that a cover member 20 is pressed into the receiving rim 21a of a recessed disk-like section 21 of dispenser 19 to provide a sealed, sanitary casing for spool 17 and its contents. Spool 17 advantageously has a groove 17a that is V-shaped in cross-section for receiving the first part of the first loop of the chain of loops to be wound thereon. The V is narrow enough to wedge the first loop 17b and allow the pulling of the first and succeeding loops around the spool as it is loaded. When the last loop (the first loop to be wound on the spool) is pulled from the spool, the loop is released from the V-shaped groove, since it is pulled in a radial direction from the spool.

Figure 4:
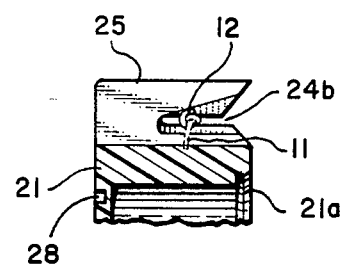

Dispensing is provided for by passing the terminal loop link, designated 22 in FIG. 3, through an opening 23 in the circumferential wall of dispenser section 21 and by then placing its knot-embraced end into an open, V-shaped slot 24 formed in a loop link separator 25. Such slot 24 is convergent friom an entry mouth 24a, so a knot 12 (or 16) joining terminal loop link 22 to the next loop link 11 of the chain will catch in the convergent end 24b, FIG. 4, of V-slot 24 and be held there while terminal loop link 22 is pulled free of such next link 11 in chain 10 as wound on spool 17.

After the terminal loop link 22 of the chain has been pulled free for use, the next loop link 11 becomes the terminal link and remains in place, with its knot 14 or 16 caught in convergent end 24b of V-slot 24, until a user of dental floss desired to remove another loop length from the chain for use. Such user then grasps the then terminal loop link 11 and pulls it sideways to free the caught knot 12 or 16 and permit pulling of an additional loop length through opening 23. While pulling the loop length, the user reinserts the loop 11 into V-slot 24 and pulls to the left until the embracing knot of the next loop link 11 is caught by convergent end 24b of such V-slot, allowing that then-terminal loop link to be pulled free of the chain.

Figure 6:
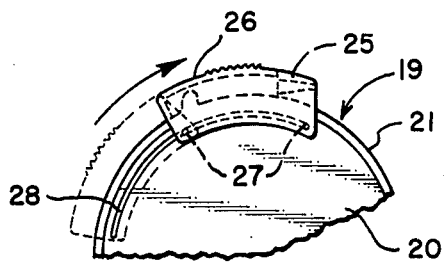

To protectively cover the terminal loop links of chain 10 prior to placing them in the position of loop link 22 for detachment, it is desirable that a sliding cover member 26, FIG. 6, be provided on the portion of the circumferential periphery of dispenser 19 lying between opening 23 and loop link separator 25. Cover member 26 is being shown as being of inverse U-formation in cross-section, so as to embrace the rim of section 21 of the dispenser, with pins 27 extending therefrom into corresponding slot 28 dispenser in section 21 and in dispenser cover member 20, respectively. Thus, sliding cover member 26 can be pushed forwardly and backwardly with the aid of finger grip formations 29 to cover and uncover, respectively, the otherwise exposed portion of chain 10. In its forward position, it covers the terminal loop link 11 that awaits being grasped, lifted, and placed in V-slot 24 after terminal loop link 22 has been pulled free of the chain. Placing of such loop link 11 in the detachable position of terminal loop link 22 takes place only immediately before detachment and use; otherwise it remains covered.

It is not recommended that a user attempt to pull the knotted portion of the loop through his teeth, since normally the knot will be too large to permit it.

Whereas this invention is here illustrated and described with specific reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A dispensing chain of individual loop lengths of a narrow, easily tied, flexible material such as dental floss to be dispensed successively, comprising an elongate series of successively interconnected loop links, each being an elongate closed loop of said material having a knot formed at one end and being unknotted at the opposite end, said knot embracing the unknotted loop end next adjacent thereto in a slip fit, whereby the loop link whose unknotted loop end is thus embraced can be disengaged from the chain by merely exerting pulling force thereon while holding the embracing knot.

2. A dispensing chain according to claim 1, wherein each of the loop links and the knot thereof are formed from a single length of the flexible material turned on itself and having its open end forming the knot.

3. A dispensing chain according to claim 1, wound upon itself in a dispenser, said dispenser comprising a casing having a longitudinally convergent V-slot link separator means for catching and holding the knot as the loop link embraced by the knot is pulled.

4. A combination according to claim 3, wherein the dispenser is a closed casing having an opening through which a terminal end portion of the chain extends, followed by the V-slot member in spaced relation thereto.

5. A combination according to claim 4, wherein a sanitary cover member is fitted over the area between said opening and said V-slot member for covering and sanitarily protecting the loop links as they extend between said opening and said V-slot member.

6. A combination according to claim 5, wherein the sanitary cover member is mounted for back and forth sliding movement back from and over, respectively, the normally covered area to provide access from time to time to a loop link within said area.

7. A combination according to claim 3, wherein the chain is wound on a spool mounted for rotation within the dispenser.

8. A combination according to claim 7, wherein the spool has a receiving slot that is of V-shape in cross section.

9. A dispensing chain according to claim 1, wherein the flexible material is dental floss.

10. A method of making a dispensing chain of individual closed loops of a narrow, easily tied, flexible material, such as dental floss, comprising the steps of pressing a loop length of the flexible material into substantially rectilinear formation; loosely forming a knot in one end of the loop length; inserting an end of another so-pressed loop length into the loosely formed knot of the first loop; tightening the knot to provide a slip-free joinder between said loops; and repeating this procedure with additional loops at either or both ends of the first-joined loops until a chain of desired length is formed.

* * * * *